(12) United States Patent
Sugiyama et al.

(10) Patent No.: US 8,603,533 B2
(45) Date of Patent: Dec. 10, 2013

(54) POLYMERSOMES AND PRODUCTION METHOD THEREOF

(75) Inventors: Yuki Sugiyama, Yokohama (JP); Takashi Ohmori, Yokohama (JP); Nobuyoshi Koga, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/512,375

(22) PCT Filed: Jul. 12, 2010

(86) PCT No.: PCT/JP2010/061769
§ 371 (c)(1),
(2), (4) Date: May 29, 2012

(87) PCT Pub. No.: WO2011/065056
PCT Pub. Date: Jun. 3, 2011

(65) Prior Publication Data
US 2012/0231055 A1 Sep. 13, 2012

(30) Foreign Application Priority Data

Nov. 30, 2009 (JP) ................................. 2009-272001

(51) Int. Cl.
| | | |
|---|---|---|
| A61K 8/14 | (2006.01) | |
| A61K 8/11 | (2006.01) | |
| A61K 8/86 | (2006.01) | |
| A61K 9/14 | (2006.01) | |
| A61Q 19/00 | (2006.01) | |
| C08G 18/48 | (2006.01) | |

(52) U.S. Cl.
CPC ... *A61K 8/14* (2013.01); *A61K 8/11* (2013.01); *A61K 8/86* (2013.01); *A61K 9/14* (2013.01); *A61Q 19/00* (2013.01); *Y10S 977/773* (2013.01); *C08G 18/4833* (2013.01); *C08G 18/4837* (2013.01); *C08G 18/4854* (2013.01)
USPC .......................... 424/489; 424/78.03; 977/773

(58) Field of Classification Search
None
See application file for complete search history.

(56) References Cited

U.S. PATENT DOCUMENTS

2003/0180335 A1* 9/2003 Ohmori et al. ................. 424/401

FOREIGN PATENT DOCUMENTS

| JP | 2003-286149 | 10/2003 |
|---|---|---|
| JP | 2005-206474 | 8/2005 |
| JP | 2005-206475 | 8/2005 |
| JP | 2006-104142 | 4/2006 |
| JP | 2006-193461 | 7/2006 |
| JP | 2006-290894 | 10/2006 |
| JP | 2009-227645 | 10/2009 |
| JP | 2010-024161 | 2/2010 |

OTHER PUBLICATIONS

Patent Abstracts of Japan, Publication No. 2009-227645, twenty pages.
Patent Abstracts of Japan, Publication No. 2005-206475, twenty pages.
Patent Abstracts of Japan, Publication No. 2005-206474, twenty pages.
Patent Abstracts of Japan, Publication No. 2010-024161, twenty-six pages.
Patent Abstracts of Japan, Publication No. 2006-193461, eight pages.
Patent Abstracts of Japan, Publication No. 2006-104142, ten pages.
Patent Abstracts of Japan, Publication No. 2006-290894, twenty-three pages.
Discher, et al. "Polymer Vesicles", Science, vol. 297, Aug. 9, 2002, pp. 967-973, eight pages.
Ghoroghchian, et al. "Near-infrared-emissive polymersomes: Self-assembled soft matter for in vivo optical imaging", Proceedings of the National Academy of Sciences of the United States of America (PNAS), 2005, 102, 2922-2927, six pages.
Lee, et al. "Preparation, Stability and In Vitro Performance of Vesicles Made with Diblock Copolymers", E. Biotechnol. Bioeng., 2001, 73, 135-145, twelve pages.
Meng, et al., "Biodegradable Polymersomes as a Basis for Artificial Cells: Encapsulation, Release and Targeting", Journal of Controlled Release, 2005, 101, 187-198, twelve pages.
Hillmyer and Bates, "Synthesis and Characterization of Model Polyalkane—Poly(ethylene oxide) Block Copolymers", Macromolecules, 1996, 29, 6994-7002, ten pages.
Discher, et al., "Polymersomes: Tough Vesicles Made from Diblock Copolymers", Science, 1999, 284, 1143-1146, four pages.

* cited by examiner

*Primary Examiner* — Frederick Krass
*Assistant Examiner* — Isaac Shomer
(74) *Attorney, Agent, or Firm* — Rankin, Hill & Clark LLP

(57) ABSTRACT

It is an object of the invention to provide a polymersome excellent in the safety and feeling in use; in particular, there is no sticky feeling but there is a good refreshing feeling; and with excellent base-agent stability. A polymersome of the present invention comprises a block-type alkylene oxide derivative represented by the following formula (I) as the membrane component:

$$R^1O\text{-}[(EO)_l(AO)_m(EO)_n]\text{-}R^2 \quad (I)$$

wherein AO is an oxyalkylene group having 3 to 4 carbon atoms, EO is an oxyethylene group, m and l+n are the average addition mole numbers for the oxyalkylene group and the oxyethylene group, respectively, and $1 \leq m \leq 70$, $1 \leq l+n \leq 70$; the percentage of the oxyethylene groups with respect to the sum of the oxyalkylene groups having 3 to 4 carbon atoms and the oxyethylene groups is 20 to 80 mass %; the addition pattern of the oxyalkylene groups having 3 to 4 carbon atoms and the oxyethylene groups is block-type; and $R^1$ and $R^2$ are identical or different hydrocarbon groups having 1 to 4 carbon atoms.

18 Claims, No Drawings

POLYMERSOMES AND PRODUCTION METHOD THEREOF

RELATED APPLICATIONS

This application claims the priority of Japanese Patent Application No. 2009-272001 filed on Nov. 30, 2009, which are incorporated herein by reference.

TECHNICAL FIELD

The present invention relates to polymersomes and the production method thereof, and in particular, relates to the improvement of the base-agent stability, skin irritation, and the feeling in use.

BACKGROUND OF THE INVENTION

If a drug is microencapsulated and administered in vivo, the metabolism of the drug in vivo is suppressed, and the medicinal effect can be maintained over a long period of time. Because of such a merit, various microencapsulation technologies for active ingredients have been searched in the fields of drugs, cosmetics, food, etc. As one of these technologies, the so-called vesicles are attracting attention. The vesicles are small enclosed sacs having a bimolecular membrane structure and formed of amphiphilic substances. Because of the unique structure, the containment of active ingredients is possible, and they are attracting attention as the carrier in drug delivery system.

Numerous amphiphilic substances that form vesicles have been investigated. In particular, vesicles consisting of phospholipids derived from biological sources are called liposomes, and various studies have been carried out from the viewpoint of safety to the body. For example, there is a report that a vesicle dispersion was formed by combining a phospholipid and a specific cationic surfactant, and this was applied to cosmetics (for example, refer to Japanese Unexamined Patent Publication No. 2006-193461). However, the liposome components are mainly derived from natural sources; therefore, they are affected by pH and temperature as well as electrolytes. Thus, there are numerous restrictions in terms of stability over time.

There are also numerous reports of synthetic surfactants as other amphiphilic substances that form vesicles. In Japanese Unexamined Patent Publication No. 2006-104142, for example, the technology wherein a mono(long-chain aliphatic)tri(short-chain alkyl)ammonium salt, a di(long-chain aliphatic)di(short-chain alkyl)ammonium salt, and a higher alcohol are used has been disclosed. In recent years, vesicle compositions wherein multi-chain multi-hydrophilic group type surfactants are used have been investigated (refer to Japanese unexamined Patent Publication No. 2006-290894).

However, the technology for hair cosmetics in Japanese Unexamined Patent Publication No. 2006-104142 was sometimes unfavorable in terms of skin safety depending on the blending quantity of the cationic surfactant. In the technology in Japanese unexamined Patent Publication No. 2006-290894, an amino acid-based surfactant was used. Thus, the vesicles can be obtained by a simple method; however, the stability of the vesicles over time was not satisfactory.

In particular, the vesicles wherein amphiphilic diblock and multiblock copolymers, in which at least one block is hydrophobic and at least one block is hydrophilic, are used as the amphiphilic substance are called "polymersomes". Their excellent mechanical stability and unique chemical properties, compared with the conventional liposomes and micelles, have been attracting attention (for example, refer to Science, 2002, 297, 967-973 and Proceedings of the National Academy of Sciences of the United States of America (PNAS), 2005, 102, 2922-2927).

Polymersomes can be stably prepared by numerous technologies common to those of liposomes (for example, refer to E. Biotechnol. Bioeng., 2001, 73, 135-145). Moreover, many-micron giant vesicles and monodisperse vesicles with a diameter of 100 nanometers can be obtained by film rehydration, sonication, and extrusion.

Polymersomes are also known to have a capability not only to entrap water-soluble hydrophilic compounds (drugs, vitamins, fluorophores, etc.) inside of their aqueous cavities but also to entrap hydrophobic molecules within their thick lamellar membranes. In addition, the size, membrane thickness, and the stabilities of those synthetic vesicles can be rationally adjusted by selecting a chemical structure of the block copolymer, number average molecular weight, hydrophilic to hydrophobic volume fraction, and various intermediary preparation methods. Accordingly, polymersomes can be provided with numerous attractive characteristics that are expected to be applied to various uses in medical imaging, drug delivery, and cosmetic devices (for example, refer to Journal of Controlled Release, 2005, 101, 187-198).

Specific vesicles of PEO-PEE (polyethylene oxide-polyethylethylene) or PEO-PBD (polyethylene oxide-polybutadiene) are known to form polymersomes with a membrane thickness of improved stability (for example, about 100 nm) compared with liposomes. For example, the PEO-PEE diblock copolymer introduced by Hillmeyer and Bates (refer to Macromolecules, 1996, 29, 6994-7002), especially EO 40-EE 37 (designated OE7, where EO is an ethylene oxide monomer and EE is an ethylethylene monomer), is reported to form a very thick membrane and show higher mechanical stability compared with any natural lipid membrane (refer to Science, 1999, 284, 1143-1164).

SUMMARY OF THE INVENTION

Problem to be Resolved by the Invention

However, the structures of all the vesicles themselves are generally unstable. Thus, there has been a problem in that it is very difficult to provide the stability that is necessary for the long-term storage of cosmetics and pharmaceuticals.

If a surfactant is applied for vesicles, some stability improvement can be expected by the adjustment of the kind and blending quantity of the surfactant. On the other hand, the same component sometimes became a contributing factor to rough skin and unsatisfactory feeling in use. In recent years, much higher safety is sought for external skin preparation, and the very blending of surfactant into preparations is sometimes raised as an issue. That is, although the surfactant is an essential component for the improvement of base-agent stability, it has been virtually impossible to perfectly achieve both the improvement of stability and the skin safety and feeling in use.

The above-described amphiphilic copolymers that form a polymersome have higher molecular weights than the conventional surfactants; therefore, the stability and safety are considered to be high. However, monomers may remain in these copolymers depending upon production methods; thus a safety issue remains when applied on the skin. In addition, polymersomes consisting of these amphiphilic copolymers had a problem in that the feeling in use for the skin and hair was poor. That is, the conventional polymersomes also could not achieve both the base-agent stability and the skin safety and feeling in use.

The present invention was made in view of the above-described problems, and an object is to provide a polymersome excellent in the safety and feeling in use; in particular, there is no sticky feeling but there is a good refreshing feeling; and with excellent base-agent stability.

Means for Solving the Problem

The present inventors have studied to achieve the above-described object. As a result, the present inventors have found that a polymersome formed from an alkylene oxide derivative with a specific structure has excellent base-agent stability, the safety to the extent that a rough skin improving effect can be shown, and a non-sticky refreshing feeling in use. In addition, the present inventors have found that it is possible to blend a large amount of low-molecular highly-polar oil, which has been difficult to blend into an aqueous base in the past, into the present polymersome, thus leading to completion of the present invention.

Thus, a polymersome of the present invention comprises a block-type alkylene oxide derivative represented by the following formula (I) as the membrane component:

wherein AO is an oxyalkylene group having 3 to 4 carbon atoms, EO is an oxyethylene group, m and l+n are the average addition mole numbers for the oxyalkylene group and the oxyethylene group, respectively, and $1 \le m \le 70$, $1 \le l+n \le 70$; the percentage of the oxyethylene groups with respect to the sum of the oxyalkylene groups having 3 to 4 carbon atoms and the oxyethylene groups is 20 to 80 mass %; the addition pattern of the oxyalkylene groups having 3 to 4 carbon atoms and the oxyethylene groups is block-type; and $R^1$ and $R^2$ are identical or different hydrocarbon groups having 1 to 4 carbon atoms.

Also, it is preferable for the polymersome that the AO group of the block-type alkylene oxide derivative represented by the above formula (I) is an oxybutylene group.

Also, it is preferable for the polymersome that a water-soluble component is contained in the inner cavity.

Also, it is preferable for the polymersome that an oil component is retained in the lamellar structure.

Also, it is preferable for the polymersome that the oil component comprises a low-molecular oil and/or highly-polar oil.

Also, an external skin preparation of the present invention comprises the polymersome.

Further, a production method of a polymersome of the present invention is characterized by comprising:
(a) mixing a block-type alkylene oxide derivative represented by the following formula (I) and a water-soluble alcohol,

wherein AO is an oxyalkylene group having 3 to 4 carbon atoms, EO is an oxyethylene group, m and l+n are the average addition mole numbers for the oxyalkylene group and the oxyethylene group, respectively, and $1 \le m \le 70$, $1 \le l+n \le 70$; the percentage of the oxyethylene groups with respect to the sum of the oxyalkylene groups having 3 to 4 carbon atoms and the oxyethylene groups is 20 to 80 mass %; the addition pattern of the oxyalkylene groups having 3 to 4 carbon atoms and the oxyethylene groups is block-type; and $R^1$ and $R^2$ are identical or different hydrocarbon groups having 1 to 4 carbon atoms; and (b) dropwise adding the mixed solution into an aqueous solvent with stirring.

Also, it is preferable for the production method that the blending quantity of the block-type alkylene oxide derivative is 0.1 to 20 mass %, and the blending quantity of the water-soluble alcohol is 0.1 to 50 mass % in the process (a).

Also, it is preferable for the production method that an oil component is also mixed in the process (a).

Also, it is preferable for the production method that the blending quantity of the oil component is 0.05 to 30 mass %.

Advantageous Effects of Invention

According to the present invention, by blending a block-type alkylene oxide derivative with a specific structure, a polymersome having a rough skin improving effect; being excellent in the safety and feeling in use; in particular, there is no sticky feeling but there is a good refreshing feeling; and being excellent in the base-agent stability can be obtained by a simple method. The polymersome of the present invention can provide new functions and textures to pharmaceuticals, cosmetics, food, etc., because it is possible to blend a large amount of low-molecular highly-polar oil, which has been difficult to blend into an aqueous base in the past.

DETAILED DESCRIPTION OF THE INVENTION

The polymersome of the present invention is formed of a block-type alkylene oxide derivative having a specific structure, and this constitutes the membrane component.

The block-type alkylene oxide derivative that forms the polymersome of the present invention has a specific structure represented by the below-described formula (I).

In the above formula (I), AO is an oxyalkylene group having 3 to 4 carbon atoms, and the specific examples include an oxypropylene group, oxybutylene group, oxyisobutylene group, oxytrimethylene group, and oxytetramethylene group. Preferably it is an oxypropylene group or oxybutylene group, and especially preferably an oxybutylene group. EO represents an oxyethylene group.

In the above formula (I), m is the average addition mole number of the oxyalkylene group, $1 \le m \le 70$, and preferably $5 \le m \le 55$. The symbols l and n are the average addition mole numbers of the oxyethylene groups having 3 to 4 carbon atoms, $1 \le l+n \le 70$, and preferably $5 \le l+n \le 60$. If the oxyalkylene group having 3 to 4 carbon atoms or the oxyethylene group is 0, namely, m or l+n is 0, the smoothness due to the blending of the polymersome is poor, and a sticky feeling tends to be generated if it exceeds 70.

In the above formula (I), it is preferable that the percentage of the oxyethylene groups with respect to the sum of the oxyalkylene groups having 3 to 4 carbon atoms and the oxyethylene groups is 20 to 80 mass %. If the percentage of the oxyethylene groups is less than 20 mass %, the hydrophilicity of the block-type alkylene oxide derivative is not sufficient. If the percentage of the oxyethylene groups exceeds 80 mass %, the lipophilicity of the block-type alkylene oxide derivative is not sufficient and the desired polymersome structure may not be formed.

In addition, it is preferable that the molecular weight of the alkylene oxide derivative is 1000 to 5000. If the molecular weight is less than 1000, a sufficient amount of polymersome may not be obtained.

In the polymersome of the present invention, the compound obtained by the block-type addition of oxyalkylene groups having 3 to 4 carbon atoms and oxyethylene groups in the above formula (I) is the main component.

In the above formula (I), $R^1$ and $R^2$ are hydrocarbon groups having 1 to 4 carbon atoms, and they may be identical to or different from each other. Examples of hydrocarbon groups having 1 to 4 carbon atoms include a methyl group, ethyl group, n-propyl group, isopropyl group, n-butyl group, sec-butyl group, and tert-butyl group, and they are preferably a methyl group or ethyl group. If the hydrocarbon groups having 5 or more carbon atoms are used, the refreshing feeling during the use of the polymersome tends to be lowered.

In the block-type alkylene oxide derivative that forms the polymersome of the present invention, so far as the effect of the present invention is not undermined, both $R^1$ and $R^2$ may be hydrogen atoms, a hydrocarbon group having 1 to 4 carbon atoms and a hydrogen atom may be present in combination for $R^1$ and $R^2$, or a hydrocarbon group having 1 to 4 carbon atoms and a different kind of hydrocarbon group may be present in combination. If there are too much derivatives in which both $R^1$ and $R^2$ are hydrogen atoms or a hydrocarbon and a hydrogen atom are present in combination, a sticky feeling tends to be generated.

Such block-type alkylene oxide derivatives can be produced by publicly known methods. For example, they can be obtained by the addition polymerization of ethylene oxide and alkylene oxide having 3 to 4 carbon atoms to a compound having hydroxyl groups and the subsequent ether reaction with an alkyl halide in the presence of an alkali catalyst.

Examples of block-type alkylene oxide derivatives usable for the invention include POE(9)POP(2) dimethyl ether, POE(14)POP(7) dimethyl ether, POE(10)POP(10) dimethyl ether, POE(6)POP(14) dimethyl ether, POE(15)POP(5) dimethyl ether, POE(25)POP(25) dimethyl ether, POE(7)POP(12) dimethyl ether, POE(22)POP(40) dimethyl ether, POE(35)POP(40) dimethyl ether, POE(50)POP(40)dimethyl ether, POE(55)POP(30) dimethyl ether, POE(30)POP(34) dimethyl ether, POE(25)POP(30) dimethyl ether, POE(27)POP(14) dimethyl ether, POE(55)POP(28) dimethyl ether, POE(36)POP(41) dimethyl ether, POE(7)POP(12) dimethyl ether, POE(17)POP(4) dimethyl ether, POE(9)POB(2) dimethyl ether, POE(14)POB(7) dimethyl ether, POE(15)POB(14) dimethyl ether, POE(18)POB(17) dimethyl ether, POE(23)POB(21) diemthyl ether, POE(27)POB(25) dimethyl ether, POE(32)POB(29) dimethyl ether, POE(35)POB(32) dimethyl ether, POE(10)POB(15) dimethyl ether, POE(20)POB(28) dimethyl ether, POE(17)POB(10) dimethyl ether, POE(28)POB(17) dimethyl ether, POE(45)POB(27) dimethyl ether, POE(34)POB(14) dimethyl ether, POE(55)POB(22) dimethyl ether, POE(44)POB(12) dimethyl ether, POE(10)POP(10) diethyl ether, POE(10)POP(10) dipropyl ether, POE(10)POP(10) dibutyl ether, POE(35)POP(30) glycol, POE(35)POB(32) glycol.

The abbreviations POE, POP and POB, which are used above, respectively stand for polyoxyethylene, polyoxypropylene and polyoxybutylene. Hereinafter these abbreviations may be used.

In the following, the production method of the polymersome of the present invention will be explained.

The polymersome composition of the present invention can be produced by sufficiently mixing a block-type alkylene oxide derivative having the above-described specific structure and a water-soluble alcohol and then dropwise adding the mixed solution into an aqueous solvent with stirring.

In the production method of the present invention, the blending quantity of the block-type alkylene oxide derivative is 0.1 to 20 mass % with respect to the final polymersome composition, and more preferably 0.1 to 10 mass %. If the blending quantity of the block-type alkylene oxide derivative is less than 0.1 mass %, the blending effect may not satisfactorily be realized. If the blending quantity exceeds 20 mass %, a sticky feeling may be generated. It is also preferable to set the blending quantity of water-soluble alcohols so that it is 0.1 to 50 mass % in total with respect to the polymersome composition.

The "water-soluble alcohol" in the present invention means a water-soluble compound having alcoholic hydroxyl group(s). Examples of such water-soluble alcohols include lower alcohols, polyhydric alcohols, saccharides, and their derivatives, and one or more of these can be used.

Examples of lower alcohols include ethanol, propanol, isopropanol, isobutyl alcohol, t-butyl alcohol.

Examples of polyhydric alcohols include dihydric alcohol (e.g. dipropylene glycol, 1,3-butylene glycol, trimethylene glycol, 1,2-butylene glycol, tetramethylene glycol, 2,3-butylene glycol, pentamethylene glycol, 2-butene-1,4-diol, hexylene glycol and octylene glycol); trihydric alcohol (e.g. glycerin and trimethylol propane); tetrahydric alcohols (e.g. diglycerin, 1,2,6-hexanetriol, and pentaerythritol); pentahydric alcohols (e.g. xylitol and triglycerin); hexahydric alcohol (e.g. sorbitol and mannitol); polyhydric alcohol polymers (e.g. diethylene glycol, dipropylene glycol-triethylene glycol, polyethylene glycol, polypropylene glycol, tetraethylene glycol, diglycerin-triglycerin, tetraglycerin and polyglycerin); dihydric alcohol alkyl ethers (e.g. ethylene glycol monomethyl ether, ethylene glycol monoethyl ether, ethylene glycol monobutyl ether, ethylene glycol monophenyl ether, ethylene glycol monohexyl ether, ethylene glycol mono-2-methyl hexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether); dihydric alcohol alkyl ethers (e.g. diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (e.g. ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ethers (e.g. chimyl alcohol, selachyl alcohol, and batyl alcohol); sugar alcohols (e.g. maltotriose, mannitol, sucrose, erythritol, glucose, fructose, starch-degraded sugar, maltose, and alcohol reduced from starch-degraded sugar); Glysolid; tetrahydrofurfuryl alcohol; POE-tetrahydrofurfuryl alcohol; POP-butyl ether; POP/POE-butyl ether tripolyoxypropylene glycerin ether; POP-glycerin ether; POP-glycerin ether phosphate; and POP/POE-pentane erythritol ether; and polyglycerin.

In addition, examples of other polyhydric alcohols include polyoxyethylene methyl glucoside (Glucam E-10) and polyoxypropylene methyl glucoside (Glucam P-10).

Examples of sugars include monosaccharides, oligosaccharides and polysaccharides.

Examples of monosaccharides include trioses (e.g. D-glyceryl aldehyde and dihydroxyacetone); tetroses (e.g. D-erythrose, D-erythrulose, D-threose, and erythritol); pentoses (e.g. L-arabinose, D-xylose, L-lyxose, D-arabinose, D-ribose, D-ribulose, D-xylulose, and L-xylulose); hexoses (e.g. D-glucose, D-talose, D-psicose, D-galactose, D-fructose, L-galactose, L-mannose, and D-tagatose); heptoses (e.g. aldoheptose and heptulose); octoses (e.g. octulose); deoxy sugars (e.g. 2-deoxy-D-ribose, 6-deoxy-L-galactose, and 6-deoxy-L-mannose); amino sugars (e.g. D-glucosamine, D-galactosamine, sialic acid, aminouronic acid, and muramic acid); and uronic acids (e.g. D-glucuronic acid, D-mannuronic acid, L-guluronic acid, D-galacturonic acid, and L-iduronic acid).

Examples of oligosaccharides include sucrose, gentianose, umbelliferose, lactose, planteose, isolychnoses, alpha, alpha-trehalose, raffinose, lychnoses, umbilicin, stachyose, and verbascose.

Examples of polysaccharides include cellulose, quins seed, starch, galactan, dermatan sulfate, glycogen, gum Arabic, heparan sulfate, gum tragacanth-keratan sulfate, chondroitin, xanthane gum, guar gum, dextran, keratosulfate, locust bean gum, and succinoglycan.

In the present invention, the above water-soluble alcohol is preferably lower alcohols and polyhydric alcohols, and more preferably ethanol, dipropylene glycol, 1,3-butylene glycol and glycerin.

In the above-described production method of the polymersome composition of the present invention, the aqueous solvent means water (for example, purified water, ion-exchanged water, tap water, etc.) or an aqueous solution of water-soluble components, and it corresponds to the water phase component in the system.

Examples of water-soluble components include additives such as powders, moisturizers, thickeners and preservatives, which are normally blended in cosmetics, quasi-drugs, etc. When a water-soluble component with a high melting point is blended, it can be pre-dissolved uniformly in water by heating. However, it is preferable to use the aqueous solution, for the production of a polymersome, after the solution is allowed to return to near room temperature after the dissolution of a water-soluble component.

The inner cavity of a polymersome formed in an aqueous solvent by the above-described production method is filled with the aqueous solvent, which is the polymersome dispersion medium. Therefore, by dispersing or dissolving a drug etc., as the water-soluble component, in the aqueous solvent, a polymersome whose inner cavity contains the water-soluble component can be produced. These water-soluble components can be added into the aqueous solvent after the formation of a polymersome. It may also be possible to introduce them into the inner cavity by dispersing the formed polymersome into an aqueous solution of a water-soluble component prepared to a suitable concentration.

Moreover, oil, which is normally difficult to mix into a water phase component, can be stably blended into the polymersome of the present invention by retaining the oil component in the lamellar structure. In addition, it is considered to be possible to create products having new properties and functions by blending various oils.

The retention of an oil component into the polymersome can be achieved by adding and mixing an oil component desired to retain between the membranes when a block-type alkylene oxide derivative and a water-soluble alcohol are mixed in the production method of the polymersome.

The blending quantity of the above-described oil component is preferably set at 0.05 to 30 mass % with respect to the amount of the polymersome composition eventually obtained.

Examples of the oil components that are retained in the polymersome of the present invention include hydrocarbon oils, higher fatty acids, higher alcohols, synthetic ester oils, silicone oils, liquid fats and oils, solid fats and oils, waxes, etc., which are normally used in cosmetics, quasi-drugs, etc., and one or more kinds of oil components can be used.

In particular, the polymersome of the present invention makes it possible to stably blend a large amount of low-molecular highly-polar oil, which has been difficult to blend into a water phase component in the past. As described above, a variety of oil components can be blended in a wide range of amount. Therefore, various polymersomes can be produced according to, for example, the desired feeling in use and the desired functions such as the moisturizing effect and rough skin prevention effect by setting blending species and the blending amount, respectively.

Examples of hydrocarbon oils include liquid paraffin, dodecane, isododecane, tetradecane, isotetradecane, hexadecane, isohexadecane, eicosene, isoeicosene, tridecane, tetradecane, hydrogenated polyisobutylene, docosane, ozocerite, squalane, pristine, paraffin, ceresin, squalene, vaseline, and micro crystalline wax.

Examples of higher fatty acids include lauric acid, myristic acid, palmitic acid, stearic acid, behenic acid, oleic acid, undecylenic acid, tallic acid, isostearic acid, linoleic acid, linolenic acid, eicosapentaenoic acid (EPA), and docosahexaenoic acid (DHA).

Examples of higher alcohols include linear alcohols (e.g. lauryl alcohol, ceryl alcohol, stearyl alcohol, behenyl alcohol, myristyl alcohol, oleyl alcohol, and cetostearyl alcohol); and branched alcohols (e.g. monostearyl glycerin ether (batyl alcohol)-2-decyl tetradecinol, lanoline alcohol, cholesterol, phytosterol, hexyldodecanol, isostearyl alcohol, and octyl dodecanol).

Examples of synthetic ester oils include isopropyl myristate, cetyl octanoate, octyldodecyl myristate, isopropyl palmitate, butyl stearate, hexyl laurate, myristil myristate, decyl oleate, hexyldecyl dimethyloctanoate, cetyl lactate, myristil lactate, lanolin acetate, isocetyl stearate, isocetyl isostearate, cholesteryl hydroxy 12-stearate, ethylene glycol di-2-ethylhexanoate, dipentaerythritol fatty acid ester, N-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethylhexanoate, trimethylolpropane triisostearate, pentaerythritol tetra-2-ethylhexanoate, glycerin tri-2-ethylhexanoate, glyceryl trioctanoate, glycerin triisopalmitate, trimethylolpropane triisostearate, cetyl 2-ethyl hexanoate-2-ethylhexyl palmitate, glycerin trimyristate, tri-2-heptyl undecanoic acid glyceride, castor oil fatty acid methyl ester, oleyl oleate, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oils include chain polysiloxanes (e.g. dimethylpolysiloxane, methylphenylpolysiloxane, diphenylpolisiloxane); cyclic polysiloxanes (e.g. octamethylcyclotetrasiloxane, decamethylcyclopentasiloxane, and dodecamethylcyclohexasiloxane); silicone resins having a three-dimensional network structure; silicone rubbers; various modified silicones (e.g. amino-modified polysiloxane, polyether-modified polysiloxane, alkyl-modified polysiloxane, and fluorine-modified polysiloxane); and acrylic silicones.

Examples of liquid fats and oils include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea oil, kaya oil, rice bran oil, Chinese wood oil, Japanese wood oil (Japanese tung oil), jojoba oil, germ oil, and triglyceride.

Examples of solid fats and oils include cacao butter, coconut oil, horse fat, hardened coconut oil, palm oil, beef tallow, mutton tallow, hardened beef tallow, palm kernel oil, lard, beef bone fat, Japan wax kernel oil, hardened oil, beef foot oil, Japan wax and hardened castor oil.

Examples of waxes include bees wax, candelilla wax, cotton wax, carnauba wax, bayberry wax, insects wax, spermaceti, montan wax, rice bran wax, lanolin, kapok wax, acetylated lanolin, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether.

By the above-described production method, a polymersome can be obtained as a polymersome composition dispersed in an aqueous solvent. Such a polymersome can be suitably used as a component of cosmetics, pharmaceuticals, etc. in the form of the above-described composition. Of course, the polymersome dispersed in an aqueous solvent can be isolated for use if it is possible.

In particular, external skin preparations excellent in the safety, feeling in use, and base-agent stability can be obtained by blending the polymersome or the polymersome composition of the present invention into publicly known cosmetic and pharmaceutical bases.

In addition, the external skin preparation containing a polymersome can be produced by suitably blending, in the above-described polymersome production method, the components that are generally used in the external skin preparations, which are normal cosmetics or quasi-drugs, into the water phase or oil phase to the extent that the effect of the present invention is not undermined. Examples of the components include ionic surfactants, nonionic surfactants, thickeners, etc., and as desired, powders such as inorganic pigments and extender pigments, moisturizers, UV absorbers, chelators, preservatives, pigments, perfume, etc.

Examples of anionic surfactants include fatty acid soaps (e.g. sodium laurate, and sodium palmitate); higher alkyl sulfate ester salts (e.g. sodium lauryl sulfate, and potassium lauryl sulfate); alkyl ether sulfate ester salts (e.g. triethanolamine POE lauryl sulfate, and sodium POE lauryl sulfate); N-acyl sarcosinates (e.g. sodium lauroyl sarcosinate); salts of higher fatty acid amide sulfonates (sodium N-myristoyl-N-methyltaurate, sodium coconut oil fatty acid methyl taurate, sodium lauryl methyl taurate); phosphoric acid ester salts (e.g. sodium POE oleyl ether phosphate, and POE stearyl ether phosphate); sulfosuccinates (e.g. sodium di-2-ethylhexylsulfosuccinate, sodium monolauroylmonoethanol amide polyoxyethylene sulfosuccinate, and sodium lauryl polypropylene glycol sulfosuccinate); alkylbenzenesulfonates (e.g. sodium linear dodecylbenzenesulfonate, triethanolamine linear dodecylbenzenesulfonate, and linear dodecylbenzenesulfonic acid); higher fatty acid ester sulfonates (e.g. sodium hardened coconut oil fatty acid glycerol sulfate); N-acylglutamates (e.g. monosodium N-lauroylglutamate, disodium N-stearoylglutamate, and monosodium N-myristoyl-L-glutamate); sulfated oils (e.g. Turkey red oil); POE alkyl ether carboxylates; POE alkyl ether allyl ether carboxylates; alpha-olefinsulfonates; higher fatty acid ester sulfonates; secondary alcohol sulfates; higher fatty acid alkylol amide sulfates; sodium lauroyl monoethanol amide succinate; ditriethanolamine N-palmitoylaspartate; and sodium caseinate.

Examples of cationic surfactants include quaternary ammonium salts such as cetyl trimethyl ammonium chloride, stearyl trimethyl ammonium chloride, behenyl trimethyl ammonium chloride, behenyl dimethyl hydroxyethyl ammonium chloride, stearyl dimethyl benzyl ammonium chloride, cetyl triethyl ammonium methyl sulfate; and amide-amine compounds such as stearic acid diethylamino-ethylamide, stearic acid dimethylamino-ethylamide, palmitic acid diethylamino-ethylamide, palmitic acid dimethylamino-ethylamide, myristic acid diethylamino-ethylamide, myristic acid dimethylamino-ethylamide, behenic acid diethylamino-ethylamide, behenic acid dimethylamino-ethylamide, stearic acid diethylamino-propylamide, stearic acid dimethylamino-propylamide, palmitic acid diethylamino-propylamide, palmitic acid dimethylamino-propylamide, myristic acid diethylamino-propylamide, myristic acid dimethylamino-propylamide, behenic acid diethylamino-propylamide, and behenic acid dimethylamino-propylamide.

Examples of amphoteric surfactants include imidazoline-type amphoteric surfactants (e.g. 2-undecyl-N,N,N-(hydroxyethyl carboxymethyl)-2-imidazoline sodium salt, and 2-cocoyl-2-imidazolinium hydroxide-1-carboxyethyloxy-2-sodium salt); betaine-type amphoteric surfactants (e.g. 2-heptadecyl-N-carboxymethyl-N-hydroxyethyl imidazolinium betaine, lauryl dimethyl aminoacetate betaine, alkyl betaine, amide betaine, and sulfo betaine).

Examples of lipophilic nonionic surfactants include sorbitan fatty acid esters (e.g. sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ehylhexylate); glycerin polyglycerin fatty acids (e.g. mono-cottonseed oil fatty acid glycerin, glyceryl monoerucate, glycerin sesquioleate, glyceryl monostearate, alpha, alpha'-glyceryl oleate pyroglutamate, glyceryl monostearate monomalate); propylene glycol fatty acid esters (e.g. propylene glycol monostearate); hydrogenated castor oil derivatives; glycerin alkylathers.

Examples of hydrophilic monoionic surfactants include POE sorbitan fatty acid esters (e.g. POE-sorbitan monooleate, POE-sorbitan monostearate, POE-sorbitan trioleate, and POE-sorbitan tetraoleate); POE sorbitol fatty acid esters (e.g. POE-sorbitol monolaurate, POE-sorbitol monooleate, POE-sorbitol pentaoleate, and POE-sorbitol monostearate); POE glycerin fatty acid esters (e.g. POE-monooleates such as POE-glycerin monostearate, POE-glycerin monoisostearate, and POE-glycerin triisostearate); POE fatty acid esters (e.g. POE-distearate, POE-monodioleate, and ethylene glycol distearate); POE alkylethers (e.g. POE-lauryl ether, POE-oleyl ether, POE-stearyl ether, POE-behenyl ether, POE-2-octyl dodecyl ether, and POE-cholestanol ether); Pluronic types (e.g. Pluronic); POE/POP-alkylethers (e.g. POE/POP-ceryl ether, POE/POP-2-decyl tetradecyl ether, POE/POP-monobutyl ether, POE/POP-lanolin hydrate, and POE/POP-glycerin ether); tetraPOE/tetraPOP-ethylenediamine condensates (e.g. Tetronic); POE-castor oil/ hydrogenated castor oil derivatives (e.g. POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid); POE-beeswax/lanolin derivatives (e.g. POE-sorbitol beeswax); alkanol amides (e.g. coconut fatty acid diethanol amide, lauric acid monoethanol amide, and fatty acid isopropanol amide); POE-propylene glycol fatty acid esters; POE-alkyl amine; POE-fatty acid amide; sucrose fatty acid ester; alkyl ethoxy dimethylamine oxides; and trioleyl phosphoric acid.

Examples of thickeners include carrageenan, karaya gum, tragacanth gum, carob gum, casein, dextrin, gelatin, sodium pectate, sodium alginate, sodium polyacrylate, carboxyvinyl polymer, tamarind gum, cellulose dialkyl dimethylammonium sulfate, aluminum magnesium silicate, bentonite, hectorite, AlMg silicate (beagum); laponite, and silicic anhydride.

Examples of natural water-soluble high-molecular compounds include plant-based high-molecular compounds (e.g. tragacanth gum, carob gum, karaya gum, carrageenan, pectin, agar, algae colloid (brown alga extract), and glycyrrhizinic acid); microorganism-based high-molecular compounds (e.g. pullulan); and animal-based high-molecular compounds (e.g. collagen, casein, albumin, gelatin).

Examples of semi-synthetic water-soluble high-molecular compounds include starch type high-molecular compounds (e.g. carboxymethyl starch, methylhydroxypropyl starch); cellulose type high-molecular compounds (e.g. methyl cellulose, ethyl cellulose, methylhydroxypropyl cellulose, hydroxyethyl cellulose, sodium cellulose sulfate, hydroxypropyl cellulose, carboxymethyl cellulose, sodium carboxymethyl cellulose, crystalline cellulose, and cellulose powder); and alginic acid type high-molecular compounds (e.g. sodium alginate, and alginic acid-propylene glycol ester).

Examples of synthetic water-soluble high-molecular compounds include vinyl type high-molecular compounds (e.g. polyvinyl alcohol, polyvinyl methyl ether, polyvinylpyrrolidone, and carboxyvinyl polymer); polyoxyethylene type high-molecular compounds (e.g. polyethylene glycol 20,000, 40,000 and 60,000); acrylic type high-molecular compounds (e.g. sodium polyacrylate, polyethyl acrylate, and polyacrylamide); polyethyleneimine; and cation polymers.

Examples of powders include inorganic powders (e.g. talc, kaolin, mica, sericite, white mica, bronze mica, synthetic mica, red mica, black mica, vermiculite, magnesium carbonate, calcium carbonate, aluminum silicate, barium silicate, calcium silicate, magnesium silicate, strontium silicate, metal tungstate, magnesium, silica, zeolite, barium sulfate, calcined calcium sulfate (calcined gypsum), calcium phosphate, hydroxyapatite, ceramic powder, metal soap (e.g. zinc myristate, calcium palmitate, and aluminum stearate), and boron nitride); organic powders (e.g. polyamide resin powder (nylon powder), polyethylene powder, polymethyl methacrylate powder, polystyrene powder, styrene/acrylic acid copolymer resin powder, benzoguanamine resin powder, polytetrafluoroethylene powder, and cellulose powder); inorganic white pigments (e.g. titanium dioxide, and zinc oxide); inorganic red pigments (e.g. iron oxide (red iron oxide), and iron titanate); inorganic brown pigments (e.g. gumma-iron oxide); inorganic yellow pigments (e.g. yellow iron oxide, and ocher); inorganic black pigments (e.g. black iron oxide, and low-order titanium oxide); inorganic violet pigments (manganese violet, and cobalt violet); inorganic green pigments (e.g. chromium oxide, chromium hydroxide, and cobalt titanate); inorganic blue pigments (e.g. ultramarine blue, and iron blue); pearl pigments (e.g. titanium oxide-coated mica, titanium oxide-coated bismuth oxychloride, titanium oxide-coated talc, colored titanium oxide-coated mica, bismuth oxychloride, and fish scale flakes); metal powder pigments (e.g. aluminum powder, and copper powder); organic pigments such as zirconium, barium or aluminum lake (e.g. organic pigments such as red 201, red 202, red 204, red 205, red 220, red 226, red 228, red 405, orange 203, orange 204, yellow 205, yellow 401, and blue 404, as well as red 3, red 104, red 106, red 227, red 230, red 401, red 505, orange 205, yellow 4, yellow 5, yellow 202, yellow 203, green 3, and blue 1); and natural colorants (e.g. chlorophyll, and beta-carotene).

Examples of moisturizers include chondroitin sulfate, hyaluronic acid, mucoitin sulfate, charonin acid, atelocollagen, cholesteryl 12-hydroxystearate, sodium lactate, bile acid salts, dl-pyrrolidonecarboxylic acid salts, short-chain soluble collagen, diglycerin (EO) PO adducts, *Rosa roxburghii* extract, yarrow extract, and melilot extract.

Examples of UV absorbers include benzoic acid UV absorbers (e.g. p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid UV absorbers (e.g. homomethyl N-acetylanthranilate); salicylic acid UV absorbers (e.g. amyl salicylate, menthyl salicylate, homomethyl salicylate, octyl salicylate, phenyl salicylate, benzyl salicylate, and p-isopropanolphenyl salicylate); cinnamic acid UV absorbers (e.g. octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate)-2-ethoxyethyl p-methoxycinnamate, cyclohexyl p-methoxycinnamate, ethyl alpha-cyano-beta-phenylcinnamate-2-ethylhexyl alpha-cyano-beta-phenylcinnamate, and glyceryl mono-2-ethylhexanoyl-diparamethoxy cinnamate); benzophenone UV absorbers (e.g. -2,4-dihydroxybenzophenone-2,2'-dihydroxy-4-methoxybenzophenone-2,2'-dihydroxy-4,4'-dimethoxybenzophenone-2,2',4,4'-tetrahydroxybenzophenone-2-hydroxy-4-methoxybenzophenone-2-hydroxy-4-methoxy-4'-methylbenzophenone-2-hydroxy-4-methoxybenzophenone-5-sulfonate, 4-phenylbenzophenone-2-ethylhexyl-4'-phenylbenzophenone-2-carboxylate-2-hydroxy-4-n-octoxybenzophenone, and 4-hydroxy-3-carboxybenzophenone); 3-(4'-methylbenzylidene)-d,l-camphor; 3-benzylidene-d,l-camphor-2-phenyl-5-methylbenzoxazol-2-2'-hydroxy-5-methylphenylbenzotriazol-2-(2'-hydroxy-5'-t-octylphenyl) benzotriazol-2-(2'-hydroxy-5'-methylphenylbenzotriazol; dibenzalazine; dianisoylmethane; and 4-methoxy-4'-t-butyldibenzoylmethane; 5-(3,3-dimethyl-2-norbornylidene)-3-pentane-2-one.

Examples of chelators include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediaminehydroxyethyltriacetate.

Examples of amino acids include neutral amino acids (e.g. threonine, and cysteine); and basic amino acids (e.g. hydroxylisine). Examples of amino acid derivatives include sodium acylsarcosine (sodium lauroylsarcosine), acylglutamate, sodium acyl-beta-alanine, and glutathione.

Examples of organic amines include monoethanolamine, diethanolamine, triethanolamine, morpholine, triisopropanolamine, 2-amino-2-methyl-1,3-propanediol, and 2-amino-2-methyl-1-propanol.

Examples of polymer emulsions include acrylic resin emulsion, polyethyl acrylate emulsion, acrylic resin liquid, polyacrylalkyl ester emulsion, polyvinyl acetate resin emulsion, and natural rubber latex.

Examples of pH adjusters include buffers such as lactic acid/sodium lactate, citric acid/sodium citrate, and succinic acid/sodium succinate.

Examples of vitamins include vitamin A, B1, B2, B6, C, E and their derivatives, pantothenic acid and its derivatives, and biotin.

Examples of antioxidants include tocopherols, dibutylhydroxytoluene, butylhydroxyanisole, and gallic acid esters.

Examples of the antioxidant promoters include phosphoric acid, citric acid, ascorbic acid, maleic acid, malonic acid, succinic acid, fumaric acid, cephalin, hexametaphosphate, phytic acid, and ethylenediamine-tetraacetic acid.

Examples of other ingredients that may be incorporated include preservatives (e.g. ethylparaben, and butylparaben); antiphlogistics (e.g. glycyrrhizinic acid derivatives, glycyrrhetinic acid derivatives, salicylic acid derivatives, hinokitiol, zinc oxide, and allantoin); skin-lightening agents (e.g. placenta extract, saxifrage extract, and arbutin); various extracts (e.g. Phellodendron bark, *Coptis japonica, Lithospermum erythrorhizon, Paeonia lactiflora, Swertia japonica*, birch, sage, loquat, ginseng, aloe, *Malva sylve*, iris, grapes, dove wheat, luffa, lily, saffron, *Cnidium officinale, shengjiang, Hypericum erectum, Ononis spinosa*, garlic, red pepper, tangerine peel, *Angelica acutiloba*, and seaweed); activators (e.g. royal jelly, photosensitive agents, and cholesterol derivatives); blood circulation promoters (e.g. nonylic acid vanillylamide, benzyl nicotinate, beta-butoxyethyl nicotinate, capsaicin, zingerone, cantharis tincture, ichthammol, tannic acid, alphta-borneol, tocopherol nicotinate, inositol hexanicotinate, cyclandelate, cinnarizine, tolazoline, acetylcholine, verapamil, cepharanthine, and gamma-oryzanol); antiseborrheics (e.g. sulfur, and thiantol); and antiinflammatory agents (e.g. tranexamic acid, thiotaurine, and hypotaurine).

EXAMPLE

Hereinafter, the present invention will be more concretely explained by examples. The present invention is not limited by these examples. Unless otherwise stated, all the blending quantities will be expressed in mass %.

Initially, the evaluation methods used for each example and comparative example will be explained.

Evaluation (1): Polymersome Forming Ability

Whether a polymersome (vesicle structure) is formed in each obtained sample was determined by the following method. The determination criteria were as follows.

◯: Particles of 50 to 500 nm size were confirmed by the dynamic light scattering measurement, and the containment of water-soluble pigment (*) was confirmed by the absorbance measurement. Additionally, no turbidity or precipitation was observed.

X: No vesicle particles of 50 to 500 nm were confirmed by the dynamic light scattering measurement. Even when they were observed, turbidity and precipitation were observed at the same time.

(*) Containment experiment of water-soluble pigment: When the intended composition was prepared, the water-soluble pigment, bromophenol blue, was added as well as the described constituents under the conditions of pH 6 or higher. After the obtained composition was dialyzed, the absorbance measurement of the obtained dialyzate was carried out. When a distinct absorption is observed near 600 nm by the absorbance measurement, the water-soluble pigment is contained. That is, the formation of a polymersome (vesicle) structure can be confirmed.

The above-described dynamic light scattering measurement and the containment experiment are simple evaluation methods. Additionally, the polymersome and vesicle formation can also be confirmed by the presence or absence of a Maltese cross image in the polarizing microscope observation and by the observation with a transmission electron microscope.

Evaluation (2): Absence of Sticky Feeling

The actual usage test, of each test example, by 10 professional panelists was conducted for the non-stickiness on the skin during use and after use. The evaluation criteria were as follows.

⊙: 8 or more panelists recognized that there was no sticky feeling during use and after use.

◯: 6 or more and less than 8 panelists recognized that there was no sticky feeling during use and after use.

Δ: 3 or more and less than 6 panelists recognized that there was no sticky feeling during use and after use.

X: less than 3 panelists recognized that there was no sticky feeling during use and after use.

Evaluation (3): Refreshing Feeling

The actual usage test, of each test example, by 10 professional panelists was conducted for the skin refreshing feeling after use. The evaluation criteria were as follows.

⊙: 8 panelists or more recognized that there was a refreshing feeling after use.

◯: 6 or more and less than 8 panelists recognized that there was a refreshing feeling after use.

Δ: 3 or more and less than 6 panelists recognized that there was a refreshing feeling after use.

X: less than 3 panelists recognized that there was a refreshing feeling after use.

Evaluation (4): Moisturizing Effect Feeling

The actual usage test, of each test example, by 10 professional panelists was conducted for the presence or absence of a moisturizing effect feeling after 120 minutes of use. The evaluation criteria were as follows.

⊙: 8 or more professional panelists recognized that there was a moisturizing effect feeling.

◯: 6 or more and less than 8 professional panelists recognized that there was a moisturizing effect feeling.

Δ: 3 or more and less than 6 professional panelists recognized that there was a moisturizing effect feeling.

X: less than 3 professional panelists recognized that there was a moisturizing effect feeling.

Evaluation (5): Test for Rough Skin Improving Effect

The test for rough skin improving effect of each test example was conducted by 10 panelists having rough skin on the face (region: cheeks). The test method was as follows; different test samples were applied on the right and left cheeks for a week, and the effect was judged on the next day after the end of the test period. The evaluation criteria were as follows.

⊚: 8 or more panelists recognized that the rough skin was improved.
○: 6 or more and less than 8 panelists recognized that the rough skin was improved.
Δ: 3 or more and less than 6 panelists recognized that the rough skin was improved.
X: less than 3 panelists recognized that the rough skin was improved.

Evaluation (6): Skin Irritation Test

A 24-hour occlusive patch test was performed on the medial side of the upper arm of 10 panelists, and the average value was calculated based on the criteria below. The evaluation criteria were as follows.
0: No abnormality was observed.
1: Slight redness was observed.
2: Redness was observed.
3: Redness and papules were observed.

The evaluation criteria for the skin irritation test were as follows.
⊚ . . . Average value of 10 panelists: 0 or higher and lower than 0.15
○ . . . Average value of 10 panelists: 0.15 or higher and lower than 0.2
Δ . . . Average value of 10 panelists: 0.2 or higher and lower than 0.3
X . . . Average value of 10 panelists: 0.3 or higher Evaluation (7): Base-Agent Stability Immediately after the production of the polymersome composition of each test example, it was filled in a transparent glass bottle and allowed to stand at 50° C. for 4 weeks. Then, the base-agent stability was evaluated by visual observation based on the following criteria.

<Evaluation Criteria>
○: transparent or translucent
X: cloudy or separated

Polymersome compositions, for the test examples with the blending compositions listed in Table 1 below, were produced, and the evaluation tests were carried out for the above-described evaluations (1) to (7). The alkylene oxide derivative used in the example of the present application has the following structure.

$$R^1O\text{-}[(EO)_l(AO)_m(EO)_n\text{---}R^2] \quad (I)$$

(In the formula, AO is an oxyalkylene group, EO is an oxyethylene group, and m and l+n are the average addition mole numbers for the above-described oxyalkylene group and the oxyethylene group, respectively.)

Accordingly, for example, when AO of the above alkylene oxide derivative is a oxybutylene group, l+n=15, m=14, and $R^1$ and $R^2$ are methyl groups, it is represented by $(BO)_{14}(EO)_{15}$, $R^{1\text{-}2}=CH_3$.

TABLE 1

| | Example | | |
|---|---|---|---|
| | 1-1 | 1-2 | 1-3 |
| (1) $(BO)_{21}(EO)_{23}$, $R^{1\text{-}2} = CH_3$, block polymer | 1 | | |
| (2) Polyoxyethylene hydrogenated castor oil | | 1 | |
| (3) Polyoxyethylene sorbitan monooleate (20 E.O.) | | | 1 |
| (4) Glyceryl tri-2-ethylhexanoate | 0.3 | 0.3 | 0.3 |
| (5) Ethanol | 5 | 5 | 5 |
| (6) Dipropylene glycol | 3 | 3 | 3 |
| (7) Glycerin | 3 | 3 | 3 |
| (8) Citric acid | 0.01 | 0.01 | 0.01 |
| (9) Sodium citrate | 0.09 | 0.09 | 0.09 |
| (10) Chelator | Appropriate quantity | Appropriate quantity | Appropriate quantity |
| (11) Ion-exchanged water | Balance | Balance | Balance |
| Evaluation (1): Polymersome forming ability | ○ | X | X |
| Evaluation (2): Absence of sticky feeling | ⊚ | Δ | ⊚ |
| Evaluation (3): Refreshing feeling | ⊚ | Δ | ⊚ |
| Evaluation (4): Moisturizing effect feeling | ⊚ | ○ | ○ |
| Evaluation (5): Test for rough skin improving effect | ⊚ | X | X |
| Evaluation (6): Skin irritation test | ⊚ | ○ | Δ |
| Evaluation (7): Base-agent stability | ○ | ○ | X |

Production Method (1) to (5) were mixed at room temperature until a transparent one-phase state is obtained, and the obtained mixed solution was dropwise added, with stirring, into a mixed solution of (6) to (11) to obtain a composition.

As shown in Table 1, in Test Example 1-1 wherein a block-type alkylene oxide derivative was used, a polymersome was formed, and the excellent results were obtained in all the evaluations, namely, in the stability, safety, and the feeling in use.

On the other hand, in Test Examples 1-2 and 1-3 wherein a common nonionic surfactant was used instead of a block-type alkylene oxide derivative, the formation of a polymersome was not observed, and they were poor in all the evaluations compared with Test Example 1-1. In particular, the rough skin improving effect and the sticky feeling were poor in Test Example 1-2, and the base-agent stability tends to be also poor in Test Example 1-3.

Thus, it is clear that the present invention is a polymersome; which is excellent in the feeling in use, stability, and safety; obtained by using a block-type alkylene oxide derivative with a specific structure as the membrane component.

Subsequently, the above-described evaluations (1) to (7) were carried out for the test examples with the formulations shown in Table 2 below, and an alkylene oxide derivative suitable for the present invention was identified.

TABLE 2

| | Example | | | | | | | | |
|---|---|---|---|---|---|---|---|---|---|
| | 2-1 | 2-2 | 2-3 | 2-4 | 2-5 | 2-6 | 2-7 | 2-8 | 2-9 |
| (1) $(BO)_{14}(EO)_{15}$, $R^{1\text{-}2} = CH_3$, block polymer | 1 | | | | | | | | |
| (2) $(BO)_{17}(EO)_{18}$, $R^{1\text{-}2} = CH_3$, block polymer | | 1 | | | | | | | |
| (3) $(BO)_{21}(EO)_{23}$, $R^{1\text{-}2} = CH_3$, block polymer | | | 1 | | | | | | |
| (4) $(BO)_{25}(EO)_{27}$, $R^{1\text{-}2} = CH_3$, block polymer | | | | 1 | | | | | |
| (5) $(BO)_{29}(EO)_{32}$, $R^{1\text{-}2} = CH_3$, block polymer | | | | | 1 | | | | |

TABLE 2-continued

| | Example | | | | | | | | |
|---|---|---|---|---|---|---|---|---|---|
| | 2-1 | 2-2 | 2-3 | 2-4 | 2-5 | 2-6 | 2-7 | 2-8 | 2-9 |
| (6) $(BO)_{34}$, $R^{1-2} = CH_3$ | | | | | | 1 | | | |
| (7) $(BO)_{21}(EO)_{23}$, $R^{1-2} = H$, block polymer | | | | | | | 1 | | |
| (8) $(BO)_{21}(EO)_{23}$, $R^{1-2} = C_6H_{13}$, block polymer | | | | | | | | 1 | |
| (9) $(BO)_{21}(EO)_{23}$, $R^{1-2} = CH_3$, random polymer | | | | | | | | | 1 |
| (10) Glyceryl tri-2-ethylhexanoate | 0.25 | 0.25 | 0.25 | 0.25 | 0.25 | 0.25 | 0.25 | 0.25 | 0.25 |
| (11) Ethanol | 5 | 5 | 5 | 5 | 5 | 5 | 5 | 5 | 5 |
| (12) Dipropylene glycol | 5 | 5 | 5 | 5 | 5 | 5 | 5 | 5 | 5 |
| (13) Glycerin | 3 | 3 | 3 | 3 | 3 | 3 | 3 | 3 | 3 |
| (14) Citric acid | 0.01 | 0.01 | 0.01 | 0.01 | 0.01 | 0.01 | 0.01 | 0.01 | 0.01 |
| (15) Sodium citrate | 0.09 | 0.09 | 0.09 | 0.09 | 0.09 | 0.09 | 0.09 | 0.09 | 0.09 |
| (16) Chelator | Appropriate quantity | Appropriate quantity | Appropriate quantity | Appropriate quantity | Appropriate quantity | Appropriate quantity | Appropriate quantity | Appropriate quantity | Appropriate quantity |
| (17) Preservative | Appropriate quantity | Appropriate quantity | Appropriate quantity | Appropriate quantity | Appropriate quantity | Appropriate quantity | Appropriate quantity | Appropriate quantity | Appropriate quantity |
| (18) Perfume | Appropriate quantity | Appropriate quantity | Appropriate quantity | Appropriate quantity | Appropriate quantity | Appropriate quantity | Appropriate quantity | Appropriate quantity | Appropriate quantity |
| (19) Ion-exchanged water | Balance | Balance | Balance | Balance | Balance | Balance | Balance | Balance | Balance |
| Evaluation (1): Polymersome forming ability | ○ | ○ | ○ | ○ | ○ | X | ○ | ○ | X |
| Evaluation (2): Absence of sticky feeling | ◎ | ◎ | ◎ | ◎ | ◎ | X | Δ | ◎ | ◎ |
| Evaluation (3): Refreshing feeling | ◎ | ◎ | ◎ | ◎ | ◎ | X | ○ | ◎ | X |
| Evaluation (4): Moisturizing effect feeling | ◎ | ◎ | ◎ | ◎ | ◎ | ◎ | Δ | Δ | ◎ |
| Evaluation (5): Test for rough skin improving effect | ◎ | ◎ | ◎ | ◎ | ◎ | Δ | Δ | Δ | ◎ |
| Evaluation (6): Skin irritation test | ◎ | ◎ | ◎ | ◎ | ◎ | ◎ | ○ | ○ | ◎ |
| Evaluation (7): Base-agent stability | ○ | ○ | ○ | ○ | ○ | X | ○ | X | X |

Production Method (1) to (11) and (18) were mixed at room temperature until a transparent one-phase state is obtained, and the obtained mixed solution was dropwise added, with stirring, into a mixed solution of (12) to (17) and (19) to obtain a composition.

As shown in Table 2, in Test Examples 2-1 to 2-5 wherein a block polymer of BO and EO was used and $R^1$ and $R^2$ were methyl groups, a polymersome was formed, and the excellent results were obtained in all the evaluations, namely, in the stability, safety, and the feeling in use.

On the other hand, in Test Example 2-6 wherein a block-type alkylene oxide derivative consisting of only oxybutylene groups was used, a polymersome was not formed, the feeling in use and base-agent stability were poor, and the rough skin improving effect was not satisfactory.

Test Example 2-7, wherein an alkylene oxide derivative whose terminals are hydrogen atoms was blended, was not desirable in terms of the feeling in use, rough skin improving effect, and skin irritation. Test Example 2-8, wherein an alkylene oxide derivative whose terminals are hydrocarbon groups having 6 carbon atoms was blended, was not satisfactory in terms of the moisturizing effect feeling and rough skin improving effect. In Test Example 2-9 wherein a random-type alkylene oxide derivative was blended, a polymersome was not formed, and the refreshing feeling and base-agent stability were poor.

From the above results and the results of further investigation, the block-type alkylene oxide derivative in the present invention is preferably a block-type alkylene oxide derivative of oxyalkylene groups having 3 to 4 carbon atoms and the oxyethylene groups, wherein the average addition mole numbers of the oxyalkylene groups and the oxyethylene groups are $1 \leq m \leq 70$ and $1 \leq +n \leq 70$, the percentage of the oxyethylene groups with respect to the sum of the oxyalkylene groups having 3 to 4 carbon atoms and the oxyethylene groups is 20 to 80 mass %, and both terminal groups are identical or different hydrocarbon groups having 1 to 4 carbon atoms.

Next, in order to investigate the preferable blending quantity of a block-type alkylene oxide derivative with a specific structure in the production of the polymersome of the present invention, the polymersome compositions of the blending compositions listed in Table 3 were produced, and the evaluation tests were carried out for the above-described evaluations (1) to (6).

TABLE 3

|  | Example | | | | |
|---|---|---|---|---|---|
|  | 3-1 | 3-2 | 3-3 | 3-4 | 3-5 |
| (1) $(BO)_{14}(EO)_{15}$, $R^{1-2} = CH_3$, block polymer | 0.01 | 0.1 | 1 | 10 | 20 |
| (2) Glyceryl diisostearate | 0.25 | 0.25 | 0.25 | 0.25 | 0.25 |
| (3) Isohexadecane | 0.05 | 0.05 | 0.05 | 0.05 | 0.05 |
| (4) Glycerin | 3 | 3 | 3 | 3 | 3 |
| (5) Dipropylene glycol | 10 | 10 | 10 | 10 | 10 |
| (6) 1,3-butylene glycol | 2 | 2 | 2 | 2 | 2 |
| (7) Malbitol | 0.5 | 0.5 | 0.5 | 0.5 | 0.5 |
| (8) Citric acid | 0.02 | 0.02 | 0.02 | 0.02 | 0.02 |
| (9) Sodium citrate | 0.08 | 0.08 | 0.08 | 0.08 | 0.08 |
| (10) Preservative | Appropriate quantity | Appropriate quantity | Appropriate quantity | Appropriate quantity | Appropriate quantity |
| (11) Perfume | Appropriate quantity | Appropriate quantity | Appropriate quantity | Appropriate quantity | Appropriate quantity |
| (12) Chelator | Appropriate quantity | Appropriate quantity | Appropriate quantity | Appropriate quantity | Appropriate quantity |
| (13) Ion-exchanged water | Balance | Balance | Balance | Balance | Balance |
| Evaluation (1): Polymersome forming ability | X | ○ | ○ | ○ | ○ |
| Evaluation (2): Absence of sticky feeling | ◎ | ◎ | ◎ | ◎ | ○ |
| Evaluation (3): Refreshing feeling | ○ | ◎ | ◎ | ◎ | ○ |
| Evaluation (4): Moisturizing effect feeling | Δ | ◎ | ◎ | ◎ | ◎ |
| Evaluation (5): Test for rough skin improving effect | Δ | ◎ | ◎ | ◎ | ◎ |
| Evaluation (6): Skin irritation test | ◎ | ◎ | ◎ | ◎ | ◎ |

Production Method (1) to (5) and (11) were mixed at room temperature until a transparent one-phase state is obtained, and the obtained mixed solution was dropwise added, with stirring, into a mixed solution of (6) to (10), (12), and (13) to obtain a composition.

From Table 3, it was confirmed that the polymersome of the present invention has a rough skin improving effect and displays excellent safety and the feeling in use when the blending quantity of a block-type alkylene oxide derivative with a specific structure is in the range of 0.1 to 20 mass %. In particular, the moisturizing effect feeling and rough skin improving effect increased with the increase in the blending quantity of a block-type alkylene oxide derivative with a specific structure.

On the other hand, in Test Example 3-1 wherein the blending quantity of the block-type alkylene oxide derivative was 0.01 mass %, a polymersome was not formed and the moisturizing effect feeling and rough skin improving effect were not satisfactory.

From the above results, it is preferable in the present invention that the blending quantity of a block-type alkylene oxide derivative with a specific structure is 0.1 to 20 mass % with respect to the total amount of components used in the production of a polymersome composition. In particular, it is more preferable that the blending quantity is 0.1 to 10 mass % in terms of the non-sticky feeling and refreshing feeling.

Next, in order to investigate the preferable blending quantity of a water-soluble alcohol in the production of the polymersome of the present invention, the polymersome compositions of the blending compositions listed in Table 4 were produced, and the evaluation tests were carried out for the above-described evaluations (1) to (7).

TABLE 4

|  | Example | | | | | | |
|---|---|---|---|---|---|---|---|
|  | 4-1 | 4-2 | 4-3 | 4-4 | 4-5 | 4-6 | 4-7 |
| (1) $(BO)_{21}(EO)_{23}$, $R^{1-2} = CH_3$, | 1 | 1 | 1 | 1 | 1 | 1 | 1 |
| (2) Glyceryl tri-2-ethylhexanoate | 0.3 | 0.3 | 0.3 | 0.3 | 0.3 | 0.3 | 0.3 |
| (3) Dipropylene glycol | 0 | 0.1 | 1 | 5 | 10 | 50 | 60 |
| (4) Citric acid | 0.02 | 0.02 | 0.02 | 0.02 | 0.02 | 0.02 | 0.02 |
| (5) Sodium citrate | 0.08 | 0.08 | 0.08 | 0.08 | 0.08 | 0.08 | 0.08 |
| (6) Preservative | Appropriate quantity | Appropriate quantity | Appropriate quantity | Appropriate quantity | Appropriate quantity | Appropriate quantity | Appropriate quantity |
| (7) Perfume | Appropriate quantity | Appropriate quantity | Appropriate quantity | Appropriate quantity | Appropriate quantity | Appropriate quantity | Appropriate quantity |
| (8) Chelator | Appropriate quantity | Appropriate quantity | Appropriate quantity | Appropriate quantity | Appropriate quantity | Appropriate quantity | Appropriate quantity |
| (9) Ion-exchanged water | Balance | Balance | Balance | Balance | Balance | Balance | Balance |
| Evaluation (1): Polymersome forming ability | X | ○ | ○ | ○ | ○ | ○ | ○ |
| Evaluation (2): Absence of sticky feeling | ○ | ◎ | ◎ | ◎ | ◎ | ○ | X |
| Evaluation (3): Refreshing feeling | ○ | ◎ | ◎ | ◎ | ◎ | ○ | X |
| Evaluation (4): Moisturizing effect feeling | X | ◎ | ◎ | ◎ | ◎ | ○ | ○ |

TABLE 4-continued

|  | Example | | | | | | |
|---|---|---|---|---|---|---|---|
|  | 4-1 | 4-2 | 4-3 | 4-4 | 4-5 | 4-6 | 4-7 |
| Evaluation (5): Test for rough skin improving effect | ○ | ◎ | ◎ | ◎ | ◎ | ○ | ○ |
| Evaluation (6): Skin irritation test | ◎ | ◎ | ◎ | ◎ | ○ | ○ | △ |
| Evaluation (7): Base-agent stability | X | ○ | ○ | ○ | ○ | ○ | X |

Production Method (1) to (3) and (7) were mixed at room temperature until a transparent one-phase state is obtained, and the obtained mixed solution was dropwise added, with stirring, into a mixed solution of (4) to (6), (8), and (9) to obtain a composition.

As shown in Table 4, in Test Examples 4-2 to 4-6 wherein 0.1 to 50 mass % of water-soluble alcohol (dipropylene glycol) with respect to the composition was blended during production, a polymersome was formed, and the evaluations, namely the feeling in use, safety, and stability were all high.

On the other hand, in Test Example 4-1 wherein a water-soluble alcohol was not blended, not only the moisturizing effect feeling was poor, but also the formation of a polymersome was not observed and the base-agent stability was poor. In Test Example 4-7 wherein the blending quantity of the water-soluble alcohol was 60 mass %, the feeling in use such as non-stickiness and a refreshing feeling was poor, some skin irritation was generated, and the base-agent stability was also not satisfactory.

From the above results, it is preferable in the present invention that the blending quantity of the water-soluble alcohol is 0.1 to 50 mass % with respect to the total amount of components used in the production of a polymersome composition.

Next, in order to investigate the preferable blending quantity of the oil component retained in the lamellar structure of the polymersome of the present invention, the polymersome compositions of the blending compositions listed in Table 5 were produced, and the evaluation tests were carried out for the above-described evaluations (1) to (7).

Production Method (1) to (3) and (7) were mixed at room temperature until a transparent one-phase state is obtained, and the obtained mixed solution was dropwise added, with stirring, into a mixed solution of (4) to (6), (8), and (9) to obtain a composition.

As shown in Table 5, in Test Examples 5-3 to 5-6 wherein 0.05 mass % or more of the oil component (tripropylene glycol pivalate) was blended during production, the high results were obtained in all evaluations.

On the other hand, a polymersome was formed even without blending an oil component as in Test Example 5-1, and the excellent results were obtained in the feeling in use, safety, and stability. However, the moisturizing effect and rough skin improving effect, due to an oil component, were poor compared with the above-described test example. As in Test Example 5-2, a relatively high effect was displayed by blending only 0.01 mass % of the oil component. However, the blending of 0.05 to 30 mass % of the oil component was considered to be preferable to obtain a high moisturizing effect in the present invention.

Next, in order to investigate the preferable production process of the polymersome, the polymersome compositions of the blending compositions listed in Table 6 were produced, and the evaluation tests were carried out for the above-described evaluations (1) to (7).

TABLE 5

|  | Example | | | | | |
|---|---|---|---|---|---|---|
|  | 5-1 | 5-2 | 5-3 | 5-4 | 5-5 | 5-6 |
| (1) $(BO)_{17}(EO)_{18}$, $R^{1-2} = CH_3$, block polymer | 1 | 1 | 1 | 1 | 1 | 1 |
| (2) Tripropylene glycol pivalate | 0 | 0.01 | 0.05 | 0.1 | 0.3 | 0.5 |
| (3) Ethanol | 5 | 5 | 5 | 5 | 5 | 5 |
| (4) Citric acid | 0.02 | 0.02 | 0.02 | 0.02 | 0.02 | 0.02 |
| (5) Sodium citrate | 0.08 | 0.08 | 0.08 | 0.08 | 0.08 | 0.08 |
| (6) Preservative | Appropriate quantity | Appropriate quantity | Appropriate quantity | Appropriate quantity | Appropriate quantity | Appropriate quantity |
| (7) Perfume | Appropriate quantity | Appropriate quantity | Appropriate quantity | Appropriate quantity | Appropriate quantity | Appropriate quantity |
| (8) Chelator | Appropriate quantity | Appropriate quantity | Appropriate quantity | Appropriate quantity | Appropriate quantity | Appropriate quantity |
| (9) Ion-exchanged water | Balance | Balance | Balance | Balance | Balance | Balance |
| Evaluation (1): Polymersome forming ability | ○ | ○ | ○ | ○ | ○ | ○ |
| Evaluation (2): Absence of sticky feeling | ◎ | ◎ | ◎ | ◎ | ◎ | ◎ |
| Evaluation (3): Refreshing feeling | ◎ | ◎ | ◎ | ◎ | ◎ | ◎ |
| Evaluation (4): Moisturizing effect feeling | △ | ○ | ◎ | ◎ | ◎ | ◎ |
| Evaluation (5): Test for rough skin improving effect | ○ | ◎ | ◎ | ◎ | ◎ | ◎ |
| Evaluation (6): Skin irritation test | ◎ | ◎ | ◎ | ◎ | ◎ | ◎ |
| Evaluation (7): Base-agent stability | ○ | ○ | ○ | ○ | ○ | ○ |

TABLE 6

|  | Example | |
|---|---|---|
|  | 6-1 | 6-2 |
| $(BO)_{25}(EO)_{27}$, $R^{1-2}$ = $CH_3$, block polymer | 1 | 1 |
| Glyceryl tri-2-ethylhexanoate | 0.5 | 0.5 |
| Ethanol | 5 | 5 |
| Glycerin | 5 | 5 |
| Citric acid | 0.02 | 0.02 |
| Sodium citrate | 0.08 | 0.08 |
| Preservative | Appropriate quantity | Appropriate quantity |
| Perfume | Appropriate quantity | Appropriate quantity |
| Chelator | Appropriate quantity | Appropriate quantity |
| Ion-exchanged water | Balance | Balance |
| Production process* | A | B |
| Evaluation (1): Polymersome forming ability | ○ | X |
| Evaluation (2): Absence of sticky feeling | ◎ | Δ |
| Evaluation (3): Refreshing feeling | ◎ | Δ |
| Evaluation (4): Moisturizing effect feeling | ◎ | ◎ |
| Evaluation (5): Test for rough skin improving effect | ◎ | ◎ |
| Evaluation (6): Skin irritation test | ◎ | ◎ |
| Evaluation (7): Base-agent stability | ○ | X |

*Production process
A: A block-type alkylene oxide derivative, ethanol, glyceryl tri-2-ethylhexanoate, and perfume were weighed and stirred to obtain a uniform transparent mixed solution. This mixed solution was dropwise added, with stirring, to the water phase in which other components for blending were thoroughly dissolved; thus a polymersome composition was obtained.
B: A composition was obtained by weighing and stirring all the components for blending into ion-exchanged water.

As shown Table 6, in Test Example 6-1 wherein process A was used for production, a polymersome composition with a small average particle size (about 100 nm) and with a transparent to translucent appearance was obtained, and it was excellent in all the evaluations, namely evaluations (1) to (7).

In Test Example 6-2 wherein process B was used for production, an emulsion composition with a large average particle size and with a cloudy appearance was obtained, and a polymersome was not formed. The base-agent stability of Test Example 6-2 as emulsion was significantly poor compared with that in which a polymersome was formed.

In Test Example 6-2, some improvement in the moisturizing effect and rough skin improving effect was recognized by the blending of an oil component. However, the dispersion of oil in the emulsion was not sufficient; therefore, the deterioration of the feeling in use such as stickiness and a refreshing feeling was also recognized.

From the above results, in the production of the polymersome of the present invention, it is preferable to have a process in which a block-type alkylene oxide derivative with a specific structure, part or all of a water-soluble alcohol, and an oil component are thoroughly mixed, and the mixed solution is subsequently added dropwise to an aqueous solvent with stirring.

Next, in order to investigate the preferable blending quantity of the oil component in the present polymersome composition and the effect when compared with an emulsion composition, the polymersome compositions of the blending compositions listed in Table 7 were produced, and the evaluation tests were carried out for the above-described evaluations (1) to (7).

TABLE 7

|  | Example | | | | | |
|---|---|---|---|---|---|---|
|  | 7-1 | 7-2 | 7-3 | 7-4 | 7-5 | 7-6 |
| $(BO)_{21}(EO)_{23}$, $R^{1-2}$ = $CH_3$, block polymer | 1 | 1 | 1 | 1 | 1 | 1 |
| Tripropylene glycol pivalate | 0.2 | 0.5 | 1 | 0.2 | 0.5 | 1 |
| 2-ethylhexyl p-methoxycinnamate | 0.1 | 0.25 | 0.5 | 0.1 | 0.25 | 0.5 |
| Dipropylene glycol | 5 | 5 | 5 | 5 | 5 | 5 |
| Glycerin | 5 | 5 | 5 | 5 | 5 | 5 |
| Citric acid | 0.02 | 0.02 | 0.02 | 0.02 | 0.02 | 0.02 |
| Sodium citrate | 0.08 | 0.08 | 0.08 | 0.08 | 0.08 | 0.08 |
| Preservative | Appropriate quantity | Appropriate quantity | Appropriate quantity | Appropriate quantity | Appropriate quantity | Appropriate quantity |
| Perfume | Appropriate quantity | Appropriate quantity | Appropriate quantity | Appropriate quantity | Appropriate quantity | Appropriate quantity |
| Chelator | Appropriate quantity | Appropriate quantity | Appropriate quantity | Appropriate quantity | Appropriate quantity | Appropriate quantity |
| Ion-exchanged water | Balance | Balance | Balance | Balance | Balance | Balance |
| Evaluation (1): Polymersome forming ability | A | A | A | C | C | C |
| Evaluation (2): Absence of sticky feeling | ○ | ○ | ○ | — | — | — |
| Evaluation (3): Refreshing feeling | ◎ | ◎ | ◎ | ◎ | Δ | Δ |
| Evaluation (4): Moisturizing effect feeling | ◎ | ◎ | ◎ | ○ | Δ | Δ |
| Evaluation (5): Test for rough skin improving effect | ○ | ◎ | ◎ | Δ | ○ | ○ |
| Evaluation (6): Skin irritation test | ○ | ○ | ◎ | Δ | Δ | ○ |
| Evaluation (7): Base-agent stability | ◎ | ◎ | ◎ | ◎ | ◎ | ◎ |
|  | ○ | ○ | ○ | X | X | X |

*Production process
A: A block-type alkylene oxide derivative, dipropylene glycol, tripropylene glycol pivalate, 2-ethylhexyl p-methoxycinnamate, and perfume were weighed and stirred to obtain a uniform transparent mixed solution. This mixed solution was dropwise added, with stirring, to the water phase in which other components for blending were thoroughly dissolved; thus a polymersome composition was obtained.
C: Tripropylene glycol pivalate, 2-ethylhexyl p-methoxycinnamate, and perfume were weighed and stirred to obtain a uniform transparent mixed oil solution. This mixed oil solution was gradually added, with stirring, to the water phase wherein all the components for blending including a block-type alkylene oxide derivative and dipropylene glycol were thoroughly dissolved in ion-exchanged water. An emulsion composition was obtained by further emulsification and stirring with a homomixer.

As shown Table 7, in Test Examples 7-1 to 7-3 wherein process A was used for production, a polymersome composition with a transparent to translucent appearance was obtained, and they were excellent in all the evaluations, namely evaluations (1) to (7). With an increase in the blending quantity of oil, the moisturizing effect feeling and rough skin improving effect had a trend to improve.

On the other hand, in Test Examples 7-4 to 7-6 wherein process C was used for the production, an emulsion composition with a cloudy appearance was obtained. All blended oils were highly-polar oils, and the base-agent stability as emulsion was significantly poor. In Test Examples 7-4 to 7-6, similarly to the polymer composition, the moisturizing effect feeling and rough skin improving effect had a trend to improve with an increase in the blending quantity of oil. However, the emulsion stability was not sufficient, oil could not uniformly be spread on the skin, and the effect was somewhat poorer than the polymersome composition. In addition, the deterioration of the feeling in use such as stickiness and a refreshing feeling was also recognized.

From the above results, it is clear in the present invention that a large amount of highly-polar oil can be stably blended by the formation of a polymersome in which a block-type alkylene oxide derivative with a specific structure is used as the membrane component though it is not achievable in the emulsion in which the same components are used. It is also clear that a conventionally unachievable excellent feeling in use can be obtained by increasing the blending quantity of the same oil.

In the following, the formulation examples of external skin preparations in which the polymersome of the present invention is blended will be described. However, the technical scope of the present invention is not limited by these examples. The obtained external skin preparations were excellent in the safety and the feeling in use and had high base-agent stability.

Formulation Example 1: Skin Lotion

|  | (% by mass) |
| --- | --- |
| Ethanol | 10 |
| Dipropylene glycol | 1 |
| Polyethylene glycol 1000 | 1 |
| Jojoba oil | 0.01 |
| Glyceryl tri-2-ethylhexanoate | 0.5 |
| POB (21) POE (23) dimethyl ether | 0.95 |
| Sodium N-stearoyl-L-glutamate | 0.1 |
| Citric acid | 0.05 |
| Sodium citrate | 0.2 |
| Potassium hydroxide | 0.4 |
| Dipotassium glycyrrhizinate | 0.1 |
| Arginine hydrochloride | 0.1 |
| L-ascorbic acid-2-glucoside | 2 |
| *Scutellaria baicalensis* extract | 0.1 |
| *Saxifrage* extract | 0.1 |
| Nettle extract | 0.1 |
| Tranexamic acid | 1 |
| Edetate trisodium | 0.05 |
| 2-ethylhexyl p-methoxycinnamate | 0.0.1 |
| Preservative | Appropriate quantity |
| Perfume | Appropriate quantity |
| Purified water | Balance |

Production Method

POB (21) POE (23) dimethyl ether, ethanol, glyceryl tri-2-ethylhexanoate, jojoba oil, 2-ethylhexyl p-methoxycinnamate and perfume were weighed and stirred to obtain a uniform transparent mixed solution. This mixed solution was dropwise added, with stirring, to the water phase in which other components for blending were thoroughly dissolved; thus a polymersome composition was obtained.

Formulation Example 2: Hair Mist

|  | (% by mass) |
| --- | --- |
| Isohexadecane | 0.1 |
| *Camellia* oil | 0.3 |
| Ethanol | 5 |
| Glycerin | 2 |
| Dipropylene glycol | 1 |
| 1,3-butylene glycol | 1 |
| Alkyl trimethyl ammonium chloride (77%) | 0.5 |
| POB (17) POE (28) dimethyl ether | 1 |
| Preservative | Appropriate quantity |
| Purified water | Balance |
| Perfume | Appropriate quantity |

Production Process

POB (17) POE (28) dimethyl ether, ethanol, dipropylene glycol, isohexadecane, camellia oil and perfume were weighed and stirred to obtain a uniform transparent mixed solution. This mixed solution was dropwise added, with stirring, to the water phase in which other components for blending were thoroughly dissolved; thus a polymersome composition was obtained.

What is claimed is:

1. A polymersome comprising a block-type alkylene oxide derivative represented by the following formula (I) as the membrane component:

$$R^1O\text{-}[(EO)_l(AO)_m(EO)_n]\text{---}R^2 \qquad (I)$$

wherein AO is an oxybutylene group, EO is an oxyethylene group, m and l+n are the average addition mole numbers for the oxybutylene group and the oxyethylene group, respectively, and $1 \leq m \leq 70$, $1 \leq l+n \leq 70$; the percentage of the oxyethylene groups with respect to the sum of the oxybutylene groups and the oxyethylene groups is 20 to 80 mass %; and $R^1$ and $R^2$ are identical or different hydrocarbon groups having 1 to 4 carbon atoms.

2. The polymersome according to claim 1, wherein a water-soluble component is contained in an inner cavity of the polymersome.

3. The polymersome according to claim 1, wherein the membrane of the polymersome comprises a lamellar structure and an oil component is retained in the lamellar structure.

4. The polymersome according to claim 3, wherein the oil component comprises a low-molecular oil and/or highly-polar oil.

5. The polymersome according to claim 2, wherein the membrane of the polymersome comprises a lamellar structure and an oil component is retained in the lamellar structure.

6. The polymersome according to claim 1, wherein a particle size of the polymersome is 50 nm to 500 nm.

7. An external skin preparation comprising the polymersome according to claim 1.

8. An external skin preparation comprising the polymersome according to claim 2.

9. An external skin preparation comprising the polymersome according to claim 3.

10. An external skin preparation comprising the polymersome according to claim 4.

11. A production method of a polymersome comprising:
(a) mixing a block-type alkylene oxide derivative represented by the following formula (I) and a water soluble alcohol,

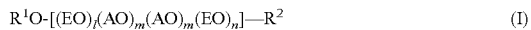

wherein AO is an oxybutylene group, EO is an oxyethylene group, m and 1+n are the average addition mole numbers for the oxybutylene group and the oxyethylene group, respectively, and $1 \leq m \leq 70$, $11+n \leq 70$; the percentage of the oxyethylene groups with respect to the sum of the oxybutylene groups and the oxyethylene groups is 20 to 80 mass %; and $R^1$ and $R^2$ are identical or different hydrocarbon groups having 1 to 4 carbon atoms; and
(b) dropwise adding the mixed solution into an aqueous solvent with stirring such that the block-type alkylene oxide derivative forms a polymersome comprising a lamellar structure.

12. The production method of a polymersome according to claim 11, wherein the blending quantity of the block-type alkylene oxide derivative is 0.1 to 20 mass %, and the blending quantity of the water-soluble alcohol is 0.1 to 50 mass % in the process (a).

13. The production method of a polymersome according to claim 11, wherein an oil component is also mixed in the process (a).

14. The production method of a polymersome according to claim 13, wherein the blending quantity of the oil component is 0.05 to 30 mass %.

15. The production method of a polymersome according to claim 12, wherein an oil component is also mixed in the process (a).

16. The production method of a polymersome according to claim 11, wherein a particle size of the polymersome is 50 nm to 500 nm.

17. The production method of a polymersome according to claim 11, further comprising:
introducing a water-soluble component into an inner cavity of the polymersome.

18. The production method of a polymersome according to claim 11, wherein the water-soluble alcohol is dipropylene glycol.

* * * * *